United States Patent
Zieske et al.

(10) Patent No.: US 7,053,059 B2
(45) Date of Patent: May 30, 2006

(54) DIALYSIS SOLUTIONS WITH REDUCED LEVELS OF GLUCOSE DEGRADATION PRODUCTS

(75) Inventors: Paul Zieske, Glenview, IL (US); Leo Martis, Long Grove, IL (US); Carolyn Choo, Lincolnshire, IL (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 0 days.

(21) Appl. No.: 10/628,065

(22) Filed: Jul. 25, 2003

(65) Prior Publication Data

US 2005/0020507 A1 Jan. 27, 2005

(51) Int. Cl.
*A61K 31/70* (2006.01)
(52) U.S. Cl. ..................................... 514/23
(58) Field of Classification Search .............. 514/23

See application file for complete search history.

(56) References Cited

U.S. PATENT DOCUMENTS

| | | | |
|---|---|---|---|
| 4,604,379 A | 8/1986 | Twardowski et al. |
| 4,663,289 A | 5/1987 | Veech |
| 4,879,280 A | 11/1989 | Seyffart et al. |
| 4,880,629 A | 11/1989 | Okamoto et al. |
| 4,886,789 A | 12/1989 | Milner |
| 4,906,616 A | 3/1990 | Gilchrist et al. |
| 4,959,175 A | 9/1990 | Yatzidis |
| 4,976,683 A | 12/1990 | Gauthier et al. |
| 5,011,826 A | 4/1991 | Steudle et al. |
| 5,039,609 A | 8/1991 | Klein |
| 5,431,496 A | 7/1995 | Balteau et al. |
| 5,436,232 A | 7/1995 | Forster et al. |
| 5,536,469 A | 7/1996 | Jonsson et al. |
| 5,780,438 A | 7/1998 | Gilchrist et al. |
| 5,869,444 A | 2/1999 | Klein |
| 6,039,719 A | 3/2000 | Wieslander et al. |
| 6,077,836 A | 6/2000 | Milner |
| 6,083,935 A | 7/2000 | Wu et al. |
| 6,214,802 B1 | 4/2001 | Nakamura et al. |
| 6,241,943 B1 | 6/2001 | Wieslander et al. |
| 6,277,815 B1 | 8/2001 | Knerr |
| 6,284,140 B1 | 9/2001 | Sommermeyer et al. |
| 6,309,673 B1 | 10/2001 | Duponchelle et al. |
| 6,429,294 B1 | 8/2002 | Masuda et al. |
| 6,492,336 B1 | 12/2002 | Mahiout |
| 2002/0144946 A1 | 10/2002 | Drauz et al. |
| 2002/0187940 A1 | 12/2002 | Masuda et al. |
| 2003/0044513 A1 | 3/2003 | Shah et al. |

FOREIGN PATENT DOCUMENTS

| | | |
|---|---|---|
| EP | 0 076 355 A2 | 4/1983 |
| EP | 0 115 911 B2 | 8/1984 |
| EP | 0 153 164 B1 | 8/1985 |
| EP | 0 170 275 B1 | 2/1986 |
| EP | 0 199 357 B1 | 10/1986 |
| EP | 0 207 676 B1 | 1/1987 |
| EP | 0 218 900 B1 | 4/1987 |
| EP | 0 270 545 B1 | 6/1988 |
| EP | 0 277 868 B1 | 8/1988 |
| EP | 0 347 714 A2 | 12/1989 |
| EP | 0 593 590 B1 | 4/1994 |
| EP | 0 602 585 B1 | 6/1994 |
| EP | 0 845 970 B1 | 6/1998 |
| EP | 0 859 621 B1 | 8/1998 |
| EP | 0 951 915 A2 | 10/1999 |
| EP | 0 958 832 A2 | 11/1999 |
| EP | 0 980 685 A2 | 2/2000 |
| EP | 1 008 341 A1 | 6/2000 |
| EP | 1 354 607 A1 | 10/2003 |
| JP | 7-252137 | 10/1995 |
| JP | 2000-37452 | 2/2000 |
| JP | 2000-245826 | 9/2000 |
| JP | 2002-282354 | 10/2002 |
| WO | WO 86/00229 | 1/1986 |
| WO | WO 93/09820 | 5/1993 |
| WO | WO 95/33477 | 12/1995 |
| WO | WO 97/06810 | 2/1997 |
| WO | WO 97/30694 | 8/1997 |
| WO | WO 99/01144 | 1/1999 |
| WO | WO 00/23086 | 4/2000 |
| WO | WO 01/26649 | 4/2001 |
| WO | WO 01/28544 | 4/2001 |
| WO | WO 02/81005 | 10/2002 |
| WO | WO 02/83739 | 10/2002 |
| WO | WO 03/13553 | 2/2003 |

OTHER PUBLICATIONS

Zheng et al., Heat sterilization of peritoneal dialysis solutions influences ingestive behavior in non-uremic rats, Kidney International, vol. 62 (2002), pp. 1447-1453.
US 4,770,879, 09/1988, Okamoto et al. (withdrawn)

*Primary Examiner*—Elli Peselev
(74) *Attorney, Agent, or Firm*—Paula J. F. Kelly; Robert M. Barrett; Joseph P. Reagen (57) ABSTRACT

Dialysis solutions with enhanced biocompatibility are provided. The dialysis solutions include a first acidic solution and a second acidic solution that are admixed to form a ready-to-use dialysis solution with reduced levels of glucose degradation products prior to use. The first acidic solution includes a dextrose concentrate, and the second acidic solution includes a buffer concentrate, such as a lactate-based buffer. The first and second acid solutions are separately sterilized prior to mixing to form the ready-to-use dialysis solutions. The dialysis solutions can be used in a variety of different applications, such as infusion into a patient during peritoneal dialysis.

38 Claims, 4 Drawing Sheets

DIALYSIS SOLUTIONS WITH REDUCED LEVELS OF GLUCOSE DEGRADATION PRODUCTS

BACKGROUND OF THE INVENTION

The present invention relates generally to medical treatments. More specifically, the present invention relates to solutions used for dialysis therapy.

Due to disease, insult or other causes, a person's renal system can fail. In renal failure of any cause, there are several physiological derangements. The balance of water, minerals and the excretion of daily metabolic load are no longer possible in renal failure. During renal failure, toxic end products of nitrogen metabolism (e.g., urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

Hemodialysis, hemofiltration and peritoneal dialysis are three types of dialysis therapies generally used to treat loss of kidney function. Hemodialysis treatment removes waste, toxins and excess water directly from the patient's blood. The patient is connected to a hemodialysis machine and the patient's blood is pumped through the machine. For example, needles or catheters can be inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood to infuse back into the patient. A large amount of dialysate, for example about 90–120 liters, is used by most hemodialysis machines to dialyze the blood during a single hemodialysis therapy. The spent dialysate is then discarded. Hemodialysis treatment lasts several hours and is generally performed in a treatment center about three times per week.

Hemofiltration is a convection-based blood cleansing technique. Blood access can be venovenous or arteriovenous. As blood flows through the hemofilter, a transmembrane pressure gradient between the blood compartment and the ultrafiltrate compartment causes plasma water to be filtered across the highly permeable membrane. As the water crosses the membrane, it convects small and large molecules across the membrane and thus cleanses the blood. An excessive amount of plasma water is eliminated by filtration. Therefore, in order to keep the body water balanced, fluid must be substituted continuously by a balanced electrolyte solution (replacement or substitution fluid) infused intravenously. This substitution fluid can be infused either into the arterial blood line leading to the hemofilter (predilution) or into the venous blood line leaving the hemofilter.

Peritoneal dialysis utilizes a sterile dialysis solution or "dialysate", which is infused into a patient's peritoneal cavity and into contact with the patient's peritoneal membrane. Waste, toxins and excess water pass from the patient's bloodstream through the peritoneal membrane and into the dialysate. The transfer of waste, toxins, and excess water from the bloodstream into the dialysate occurs due to diffusion and osmosis during a dwell period as an osmotic agent in the dialysate creates an osmotic gradient across the membrane. The spent dialysate is later drained from the patient's peritoneal cavity to remove the waste, toxins and excess water from the patient.

There are various types of peritoneal dialysis therapies, including continuous ambulatory peritoneal dialysis ("CAPD") and automated peritoneal dialysis. CAPD is a manual dialysis treatment, in which the patient connects the catheter to a bag of fresh dialysate and manually infuses fresh dialysate through the catheter or other suitable access device and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient drains the spent dialysate and then repeats the manual dialysis procedure. Tubing sets with "Y" connectors for the solution and drain bags are available that can reduce the number of connections the patient must make. The tubing sets can include pre-attached bags including, for example, an empty bag and a bag filled with dialysate.

In CAPD, the patient performs several drain, fill, and dwell cycles during the day, for example, about four times per day. Each treatment cycle, which includes a drain, fill and dwell, takes about four hours.

Automated peritoneal dialysis is similar to continuous ambulatory peritoneal dialysis in that the dialysis treatment includes a drain, fill, and dwell cycle. However, a dialysis machine automatically performs three or more cycles of peritoneal dialysis treatment, typically overnight while the patient sleeps.

With automated peritoneal dialysis, an automated dialysis machine fluidly connects to an implanted catheter. The automated dialysis machine also fluidly connects to a source or bag of fresh dialysate and to a fluid drain. The dialysis machine pumps spent dialysate from the peritoneal cavity, through the catheter, to the drain. The dialysis machine then pumps fresh dialysate from the dialysate source, through the catheter, and into the patient's peritoneal cavity. The automated machine allows the dialysate to dwell within the cavity so that the transfer of waste, toxins and excess water from the patient's bloodstream to the dialysate solution can take place. A computer controls the automated dialysis machine so that the dialysis treatment occurs automatically when the patient is connected to the dialysis machine, for example, when the patient sleeps. That is, the dialysis system automatically and sequentially pumps fluid into the peritoneal cavity, allows for dwell, pumps fluid out of the peritoneal cavity, and repeats the procedure.

Several drain, fill, and dwell cycles will occur during the treatment. Also, a final volume "last fill" is typically used at the end of the automated dialysis treatment, which remains in the peritoneal cavity of the patient when the patient disconnects from the dialysis machine for the day. Automated peritoneal dialysis frees the patient from having to manually perform the drain, dwell, and fill steps during the day.

In general, standard peritoneal dialysis solutions contain dextrose at a concentration of 1.5% to 4.25% by weight to effect transport of water and metabolic waste products across the peritoneal membrane. Dextrose is generally recognized as a safe and effective osmotic agent, particularly for short dwell exchanges. Dextrose-based peritoneal dialysis solutions are typically formulated at a pH of 5.0 to 5.5. This is to avoid discomfort and/or pain during infusion without excessive degradation of dextrose.

Figure 1:
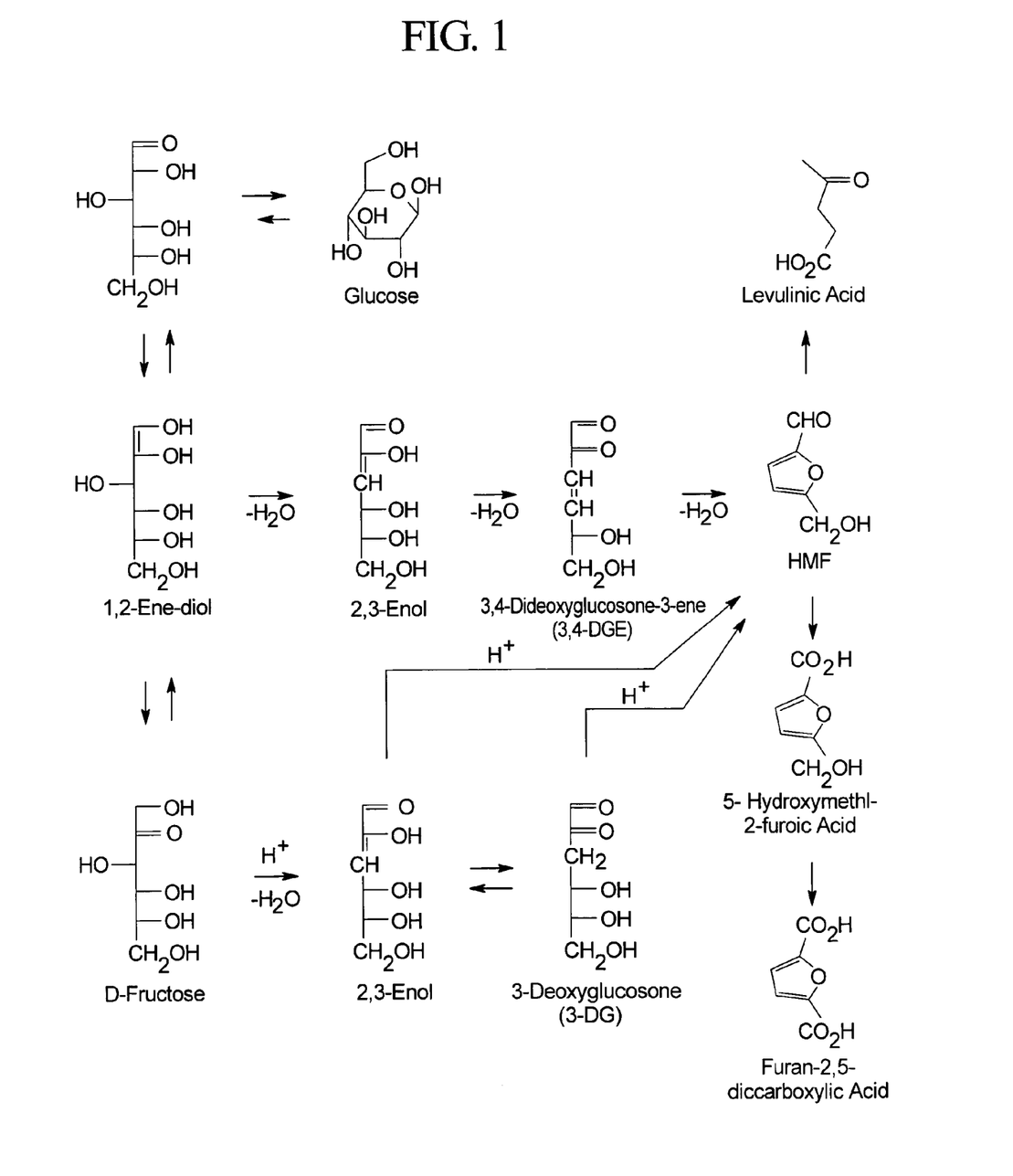
FIG. 1 is a schematic representation of non-oxidative reaction pathways that illustrate the degradation of glucose and products thereof.
Figure 2:
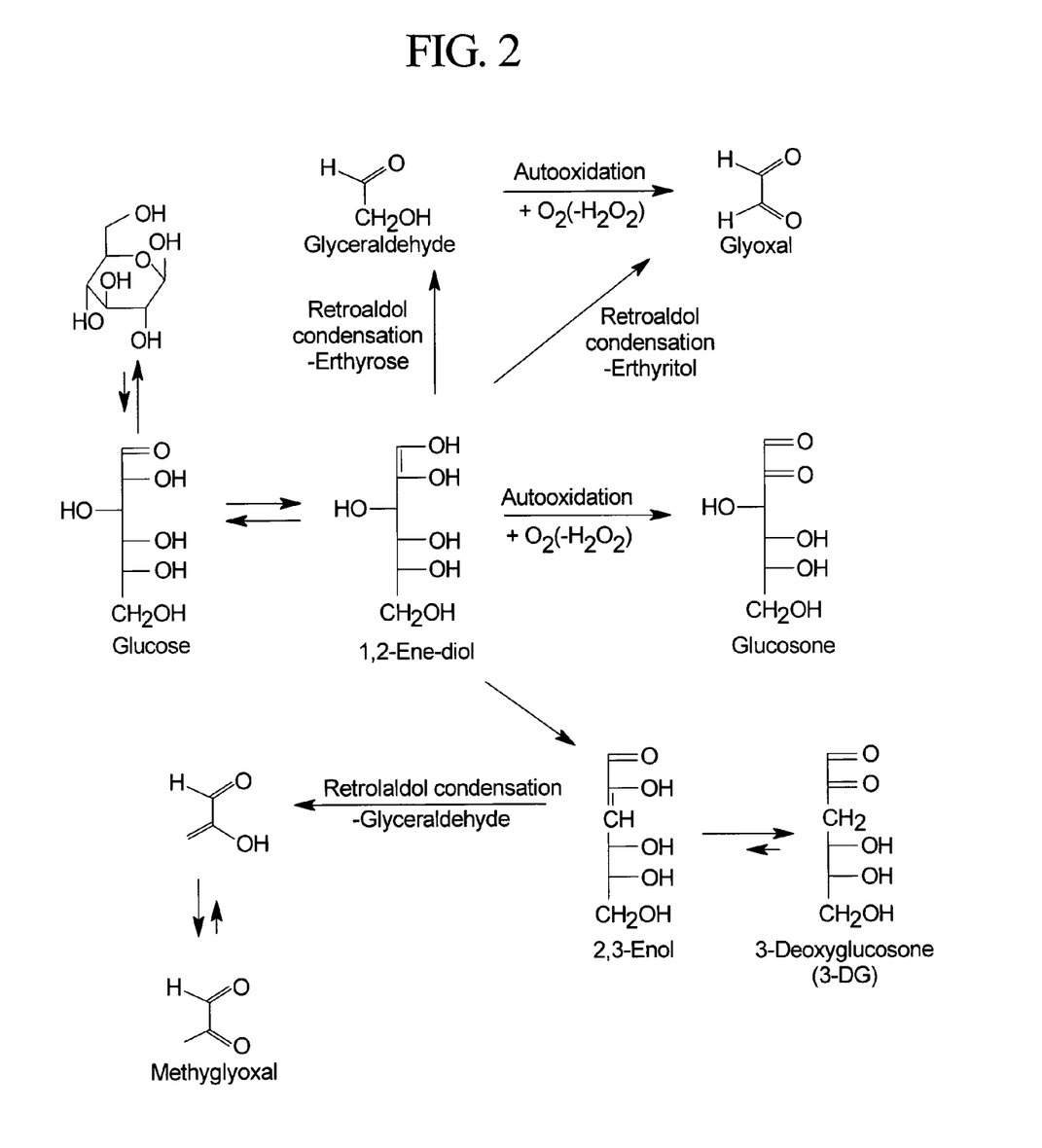
FIG. 2 is a schematic representation of autooxidation reaction pathways that illustrate the degradation of glucose and products thereof.

However, at this pH dextrose can undergo significant degradation, thus resulting in a number of reaction products commonly referred to as glucose degradation products ("GDPs") and as illustrated in FIGS. 1 and 2. It has been found that GDPs can alter the function of peritoneal cells, thus impairing host defense. If the host defense is compromised, this can contribute to frequent occurrences of peritonitis observed in the patient population. In addition, GDPs can lead to the formation of advanced glycation end products (AGEs). AGEs are believed to damage the peritoneal membrane to such an extent that peritoneal dialysis can no longer be effectively utilized to sustain life in kidney disease patients.

A need, therefore, exists for dialysis solutions, such as peritoneal dialysis solutions, that have improved biocompatible characteristics.

SUMMARY OF THE INVENTION

The present invention generally relates to dialysis solutions. At least two parts of the dialysis solutions are separately formulated. A first part includes a dextrose concentrate and a second part include a buffer concentrate. The first and second parts are separately sterilized at an acidic pH and then admixed prior to use, such as infusion into a patient during peritoneal dialysis. The dialysis solutions of the present invention have enhanced biocompatible characteristics, such as reduced levels of glucose degradation products (GDPs).

For example, Applicants have demonstrated that GDP levels can be reduced by sterilizing the dextrose concentrate at reduced pH levels. Once sterilized, the dextrose concentrate and the buffer concentrate can be combined to form a ready-to-use dialysis solution with reduced levels of GDPs. As previously discussed, GDPs can alter the function of peritoneal cells, and thus can contribute to the occurrence of peritonitis during peritoneal dialysis.

In an embodiment, the present invention provides a dialysis solution. The dialysis solution includes a first acidic solution and a second acidic solution wherein the first and second acidic solutions are admixed to form a ready-to-use dialysis solution. The first acidic solution at least includes a dextrose concentrate that includes, for example, dextrose, calcium chloride and magnesium chloride. The second acidic solution includes a buffer concentrate, such as a lactate-based buffer.

In an embodiment, the dextrose concentrate includes about 30.0 g/L to about 85.0 g/L of dextrose. The dextrose concentrate further includes, for example, calcium chloride dihydrate, magnesium chloride hexahydrate, the like and any suitable combinations thereof. Preferably, the dextrose concentrate includes about 5.0 mEq/L to about 7.0 mEq/L of calcium.

In an embodiment, the ready-to-use dialysis solution includes about 1.5% to about 4.25% of dextrose. The ready-to-use dialysis solution further includes, for example, sodium, calcium, magnesium, chloride, lactate, the like and any suitable combinations thereof.

In another embodiment, the present invention provides a two part peritoneal dialysis solution that includes a first part and a second part admixed prior to infusion into a patient. The first part includes an acidic concentrate that includes dextrose. The second part includes a lactate-based buffer concentrate that has a pH of less than 7.0.

In an embodiment, the first part has a pH that ranges from about 2.8 to about 3.8, preferably from about 3.0 to about 3.5.

In yet another embodiment, the present invention provides a two part peritoneal dialysis solution that includes a first part housed in a first structure and a second part housed in a second structure. The first part includes an acidic dextrose concentrate. The second part includes an acidic buffer concentrate that includes, for example, a lactate-based concentrate at a pH less than about 5.5. The first part and the second part are separately sterilized and admixed to form a ready-to-use peritoneal dialysis solution.

In an embodiment, the first part and the second part are stored in a multi-chamber container that includes the first structure and the second structure adaptedly coupled such that the first part and the second part are capable of mixing to form the mixed solution prior to infusion into the patient.

In an embodiment, the first structure and the second structure each include a solution bag each capable of being coupled to an admix device allowing mixing of the first part and the second part to form the mixed solution.

In a further embodiment, the present invention provides a method of modifying a standard dialysis solution. This includes formulating two or more solution parts of the standard dialysis solution wherein the solution parts at least include a dextrose concentrate and a buffer concentrate. The dextrose and buffer concentrates are separately sterilized at a pH of less than 7.0 and then mixed to produce a modified standard dialysis solution.

In an embodiment, the modified standard dialysis solution includes fewer glucose degradation products than the standard dialysis solution. The glucose degradation products can include, for example, 5-hydroxymethyl furfural, 3-deoxyglucosone, glyoxal, methylglyoxal, acetaldehyde, the like and combinations thereof. The modified standard dialysis solution can include a solution composition that is substantially the same as the standard dialysis solution except for the glucose degradation products.

In still a further embodiment, the present invention provides a method of providing dialysis to a patient. The method includes mixing an acidic solution that includes a dextrose concentrate and an acidic buffer solution that includes, for example, a lactate-based buffer concentrate. The acidic solution and the buffer solution are separately sterilized and then admixed to form a ready-to-use dialysis solution.

The dialysis solutions of the present invention can be applied in a variety of different and suitable dialysis therapies, such as peritoneal dialysis. In an embodiment, the dialysis solutions, once mixed, can be infused into a patient during continuous ambulatory peritoneal dialysis, automated peritoneal dialysis or the like.

An advantage of the present invention is to provide improved dialysis solutions.

Another advantage of the present invention is to provide dialysis solutions with improved biocompatible characteristics.

Yet another advantage of the present invention is to provide dialysis solutions with reduced levels of glucose degradation products.

Still yet another advantage of the present invention is to provide improved dialysis solutions that include separately formulated and sterilized acidic solution parts.

A further advantage of the present invention is to provide a lactate-buffered dialysis solution with reduced glucose degradation products.

A still further advantage of the present invention is to provide methods of reducing glucose degradation products in dextrose-based solutions.

Still yet a further advantage of the present invention is to provide improved methods of making and using dialysis solutions.

Moreover, an advantage of the present invention is to provide methods of modifying dialysis solutions to produce dialysis solutions that have reduced levels of glucose degradation products.

Additional features and advantages of the present invention are described in, and will be apparent from, the following Detailed Description of the Invention and the figures.

DETAILED DESCRIPTION OF THE INVENTION

The present invention generally relates to dialysis solutions. In particular, the present invention relates to dialysis solutions with enhanced biocompatible properties, such as with reduced levels of glucose degradation products and methods of making and using same.

Dextrose (α-D-glucose) is known to decompose into decomposition products commonly referred to as glucose degradation products (GDPs) during sterilization, such as autoclaving, steam sterilization or the like. Examples of GDPs can include 5-hydroxymethyl furfural (5-HMF), 3-deoxyglucasone, glyoxal, methylglyoxal, acetaldehyde, the like and as illustrated in FIGS. 1 and 2. GDPs can damage the peritoneal membrane and thus can have an adverse effect on peritoneal dialysis.

Applicants have discovered that the level of GDPs can be reduced in dialysis solutions. In general, the parts of a dialysis solution are separately formulated and sterilized prior to mixing. The solution parts at least include a first acid solution and a second acid solution that are admixed to form a ready-to-use dialysis solution. The first acid solution includes a dextrose concentrate, and the second acid solution includes a buffer concentrate, such as a lactate-based buffer. Applicants have demonstrated that the level of GDPs in the acidic dextrose concentrate after sterilization can be reduced by decreasing the solution pH as described in detail below. Thus, when the dextrose concentrate is mixed with the buffer concentrate after sterilization, a dialysis solution can be formed that has a reduced level of glucose degradation products. In an embodiment, the level of glucose degradation products in the dialysis solutions of the present invention is less than the level of glucose degradation products in standard dialysis solutions.

The dialysis solutions of the present invention can be used in a variety of suitable applications. Preferably, the dialysis solutions are used during peritoneal dialysis, such as during automated peritoneal dialysis.

However, it should be appreciated that the present invention can be used in a variety of different and suitable dialysis therapies to treat kidney failure. Dialysis therapy as the term or like terms are used throughout the text is meant to include and encompass any and all suitable forms of therapies that utilize the patient's blood to remove waste, toxins and excess water from the patient. Such therapies, such as hemodialysis, hemofiltration and hemodiafiltration, include both intermittent therapies and continuous therapies used for continuous renal replacement therapy (CRRT). The continuous therapies include, for example, slow continuous ultrafiltration (SCUF), continuous venovenous hemofiltration (CVVH), continuous venovenous hemodialysis (CVVHD), continuous venovenous hemodiafiltration (CVVHDF), continuous arteriovenous hemofiltration (CAVH), continuous arteriovenous hemodialysis (CAVHD), continuous arteriovenous hemodiafiltration (CAVHDF), continuous ultrafiltration periodic intermittent hemodialysis or the like. Preferably, the dialysis solutions are used during peritoneal dialysis, such as automated peritoneal dialysis, continuous ambulatory peritoneal dialysis, continuous flow peritoneal dialysis and the like. Further, although the present invention, in an embodiment, can be utilized in methods providing a dialysis therapy for patients having chronic kidney failure or disease, it should be appreciated that the present invention can be used for acute dialysis needs, for example, in an emergency room setting. Lastly, as one of skill in the art appreciates, the intermittent forms of therapy (i.e., hemofiltration, hemodialysis, peritoneal dialysis and hemodiafiltration) may be used in the in center, self/limited care as well as the home settings.

As previously discussed, the present invention provides dialysis solutions with enhanced biocompatibility. In general, separately formulated and sterilized solution parts are combined to form a ready-to-use solution. In an embodiment, the dialysis solutions of the present invention include a first acidic solution part and a second acidic solution part. The first acidic solution part at least includes a dextrose concentrate wherein the second acidic solution part includes a buffer concentrate, such as a lactate-based buffer.

In an embodiment, the acidic dextrose concentrate has a pH that ranges from about 2.8 to about 3.8, preferably from about 3.0 to about 3.5, more preferably from about 3.2 to about 3.4. The dextrose concentrate can include any number and amount of different components. For example, the dextrose concentrate can include dextrose, calcium chloride, magnesium chloride, the like and combinations thereof. The dextrose concentrate can also include a pH adjusting agent. Examples of the pH adjusting agent include an inorganic acid, such as hydrochloric acid; an organic acid, such as lactic acid; the like and combinations thereof.

In an embodiment, the dextrose concentrate includes about 30.0 g/L to about 85.0 g/L of dextrose, about 0.514 g/L of calcium chloride dehydrate, about 0.102 g/L of magnesium chloride hexahydrate, the like and any suitable combinations thereof. In another embodiment, the dextrose concentrate includes about 30.0 g/L to about 85.0 g/L of dextrose, about 0.367 g/L calcium chloride dihydrate, about 0.102 g/L of magnesium chloride hexahydrate, the like and any suitable combinations thereof.

The buffer concentrate of the present invention can include any suitable number, type and amount of components. In an embodiment, the buffer concentrate includes a lactate-buffered solution, for example, a solution that includes sodium lactate, sodium chloride, the like and combinations thereof.

The buffer pH can include any suitable level effective for formulating and sterilizing the single part buffer solution and subsequently formulating a ready-to-use dialysis solution that includes a mixture of the buffer and other solution parts including an acidic dextrose concentrate. In an embodiment, the buffer pH is acidic, such as less than 7.0, less than about 5.5 or the like, such as ranging from about 5.0 to about 5.5. Preferably, the buffer pH ranges from about 5.1 to about 5.3. A pH adjusting agent can be added to the buffer solution, such as sodium hydroxide, hydrochloric acid, and/or the like.

In an embodiment, the present invention provides a method of modifying a standard dialysis solution that can include modifying any suitable standard solution, such as the standard peritoneal dialysis solutions described in detail below. The parts associated with the solution are separately formulated and sterilized at an acidic pH. This allows subsequent mixing of the solution parts to form a dialysis solution, such as a standard dialysis solution, that has been modified to include reduced levels of glucose degradation products. The separately formulated and sterilized solution parts can include an acidic dextrose concentrate and an acidic buffer concentrate, such as a lactate-based buffer at a pH less than about 5.5. In an embodiment, the modified dialysis solution has a solution composition that is substantially the same as the standard dialysis solution except for the levels of GDPs.

The dextrose concentrate and the buffer concentrate can be formulated, sterilized and admixed in any suitable manner prior to use, such as prior to infusion into a patient during peritoneal dialysis. In an embodiment, a mixed solution that includes the dextrose concentrate and the buffer concentrate has a compositional make-up that is the same as or substantially the same as compared to standard dialysis solutions, such as standard peritoneal dialysis solutions, except for the level of glucose degradation products. The proportion of dextrose concentrate to buffer concentrate in the mixed solution, in an embodiment, is about 1:1. Provided below are illustrative examples of the dialysis solutions pursuant to an embodiment of the present invention:

TABLE 1

COMPOSITION OF DEXTROSE AND BUFFER CONCENTRATES

| | Present Invention | |
|---|---|---|
| | 3.5 mEq/L calcium | 2.5 mEq/L calcium |
| Dextrose Concentrate | | |
| Dextrose, hydrous (g/L) | 30.0, 50.0 or 85.0 | 30.0, 50.0 or 85.0 |
| Calcium chloride dihydrate (g/L) | 0.514 | 0.367 |
| Magnesium chloride hexahydrate (g/L) | 0.102 | 0.102 |
| pH range at 25° C. | 2.8–3.8 | 2.8–3.8 |

TABLE 1-continued

COMPOSITION OF DEXTROSE AND BUFFER CONCENTRATES

| | Present Invention | |
|---|---|---|
| | 3.5 mEq/L calcium | 2.5 mEq/L calcium |
| Buffer Concentrate | | |
| Sodium chloride (g/L) | 10.76 | 10.76 |
| Sodium L-lactate (g/L) | 8.96 | 8.96 |
| pH range at 25° C. | 5.0–5.5 | 5.0–5.5 |

TABLE 2

COMPARATIVE DIALYSIS SOLUTION DATA

| Component | Present Invention* | Standard Solution |
|---|---|---|
| Dextrose, hydrous (%) | 1.5, 2.5, or 4.25 | 1.5, 2.5, or 4.25 |
| Sodium (mEq/L) | 132 | 132 |
| Calcium (mEq/L) | 2.5[a] or 3.5[b] | 2.5[a] or 3.5[b] |
| Magnesium (mEq/L) | 0.50 | 0.50 |
| Chloride (mEq/L) | 95[c] | 95[c] |
| Lactate (mEq/L) | 40 | 40 |
| pH at 25° C. | 4.0–6.5 | 4.0–6.5 |
| Target pH at infusion | 5.2 | 5.2 |

*Final mixed solution
[a]2.5 mEq/L calcium formulation
[b]3.5 mEq/L calcium formulation
[c]value is for 2.5 mEq/L calcium; 1 mEq/L higher for 3.5 mEq/L calcium formulations Applicants have conducted a number of experiments that demonstrate the effects of solution pH on GDPs as described in detail below:

EXPERIMENT ONE

In this experiment, the pH was adjusted with hydrochloric acid in a 10.65% dextrose solution to determine changes in glucose degradation products based upon changes in solution pH. The test solutions were sterilized in glass bottles and contained electrolyte components, such as magnesium chloride and calcium chloride, similar to standard dextrose—containing solutions and the dextrose concentrates made pursuant to an embodiment of the present invention discussed above.

Figure 3:
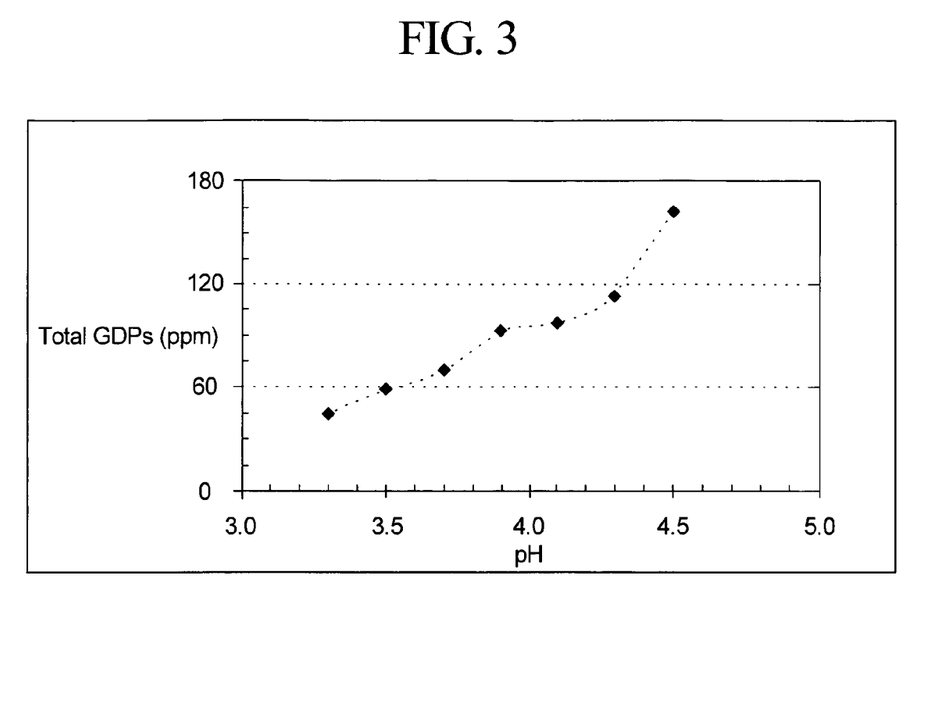
FIG. 3 is a graphical representation showing the effect of solution pH on glucose degradation pursuant to an embodiment of the present invention.

Solutions with added hydrochloric acid were stable in terms of pH before and after sterilization. As the pH was lowered to about 3.3, the level of GDPs formed during sterilization decreased with decreasing pH levels as shown in FIG. 3. The total GDPs were measured and determined as a sum of the levels of 5-hydroxymethyl furfural, 3-deoxyglucasone, glyoxal, and methylglyoxal in solution.

EXPERIMENT TWO

In this experiment, dialysis solutions at two dextrose concentrations (1.5% and 4.25%) were prepared according to an embodiment of the present invention. The GDP levels in the mixed solutions were measured and compared to the GDP levels in standard peritoneal dialysis solutions. As shown below in Table 3, the GDP levels in the peritoneal dialysis solutions prepared according to an embodiment of the present invention were significantly less than GDP levels in the standard dextrose containing solutions.

TABLE 3

COMPARATIVE GDP DATA

| Product | 5-HMF (AU at 284 nm) | Color (klett) | Acetaldehyde (ppm) | 3-DG (ppm) | Glyoxal (ppm) | Methyl-Glyoxal (ppm) | 5-HMF related GDP (at 228 nm) |
|---|---|---|---|---|---|---|---|
| Standard Solution (4.25% dextrose) | 0.022 | 8 | 6.7 | 71 | 0.4 | 0.7 | 0.032 |
| Present Invention (4.25% dextrose) | 0.013 | 3 | 1.6 | 19 | 1.0 | 0.2 | 0.028 |
| Standard Solution (1.5% dextrose) | 0.016 | 2 | 3.1 | 28 | 0.34 | 0.2 | 0.075 |
| Present Invention (1.5% dextrose) | 0.016 | 2 | 1.6 | 12 | 1.1 | 0.5 | 0.052 |

It should be appreciated that the components of the dialysis solutions of the present invention can be housed or contained in any suitable manner such that the dialysis solutions can be effectively prepared and administered. In an embodiment, the present invention includes a multi-part dialysis solution in which two or more parts are formulated and stored separately, and then mixed just prior to use. A variety of containers can be used to house the various parts of the dialysis solution, such as separate containers (i.e., flasks or bags) that are connected by a suitable fluid communication mechanism. In an embodiment, a multi-chamber container or bag can be used to house the separate components of the solution including the dextrose concentrate and the buffer concentrate. In an embodiment, the separate components are mixed within the multi-chamber bag prior to use, such as applied during continuous ambulatory peritoneal dialysis.

Figure 4:
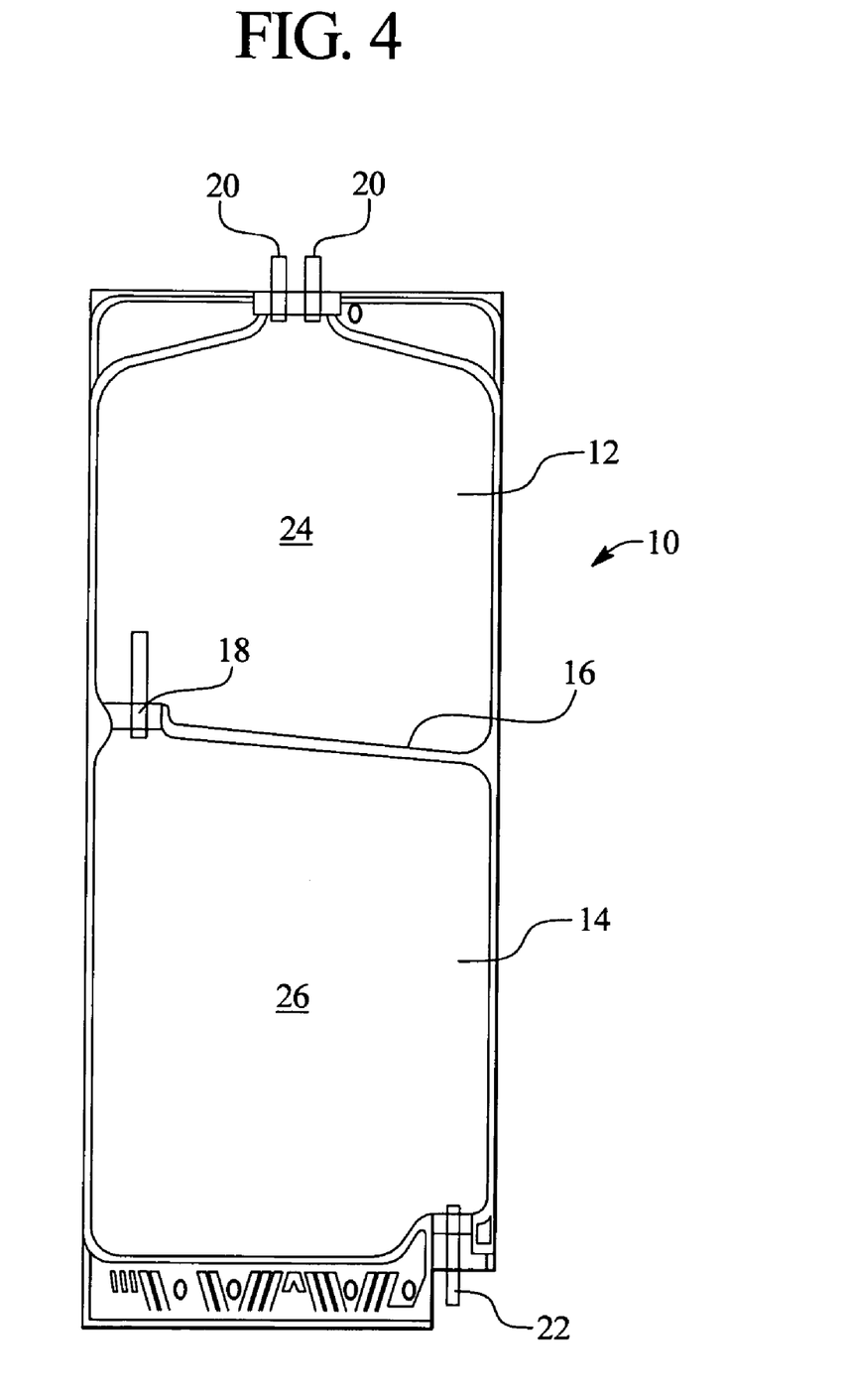
FIG. 4 is a schematic representation of a multi-chambered bag for use with the dialysis solutions pursuant to an embodiment of the present invention.

FIG. 4 illustrates a suitable container for storing, formulating, mixing and administering a dialysis solution, such as during continuous ambulatory peritoneal dialysis, according to an embodiment of the present invention. The multi-chamber bag 10 has a first chamber 12 and a second chamber 14. The interior of the container is divided by a heat seal 16 into the two chambers. It should be appreciated that the container can be divided into separate chambers by any suitable seal. In an embodiment, the container can be divided into separate chambers, such as two chambers, by a peel seal. The multi-chamber container 10 also has a frangible connector 18 to sealingly couple the first chamber 12 to the second chamber 14. To mix the solution within the multi-chamber bag 10, the frangible connector 18 is broken.

The first container or chamber 12 includes two port tubes 20 of suitable sizes and lengths. One of the port tubes, for example, can be utilized to add other constituents to the first chamber 12 during formulation of the solution of the present invention, if necessary. The remaining port tube, for example, can be utilized to adaptedly couple the first chamber 12 to the patient via a patient's administration line (not shown). The second container or chamber 14 has a single port tube 22 extending therefrom. This is closed in an embodiment by, for example, a solid rod (not shown). in this regard, it is not possible to add any additional constituents to this chamber and/or connect this chamber to a patient's administration line such that the chamber 14 cannot be adapted to deliver its constituents to the patient. When not closed, it should be appreciated that the port tube 22 can be utilized to add other constituents to the chamber 14, adaptedly coupled to a patient's administration line and/or the like.

In an embodiment, the transfer of product within the multi-chamber bag 10 can be initiated from the first chamber 12 to the second chamber 14 such that the components of each chamber can be properly mixed to form the dialysis solution of the present invention. In an embodiment, the dextrose concentrate 24 is contained in the first chamber 12 and the buffer concentrate 26 is contained in the second chamber 14.

In this regard, the first chamber 12 is smaller in volume than the second chamber 14 such that the components of each chamber can be properly mixed once the transfer from the first chamber to the second chamber has occurred. Thus, the multi-chamber bag 10 can house at least two solution component parts that after mixture will result in a ready-to-use dialysis solution. An example of the multi-chamber container is set forth in U.S. Pat. No. 5,431,496, the disclosure of which is incorporated herein by reference. The multi-chamber bag can be made from a gas permeable material, such as polypropylene, polyvinyl chloride or the like.

It should be appreciated that the multi-chamber bag can be manufactured from a variety of different and suitable materials and configured in a number of suitable ways such that the dialysis solutions of the present invention can be effectively formulated and administered to the patient during medical therapy in any suitable manner. For example, the first chamber can be larger in volume than the second chamber and further adapted such that the dialysis solution of the present invention can be readily and effectively made and administered to the patient.

Figure 5:
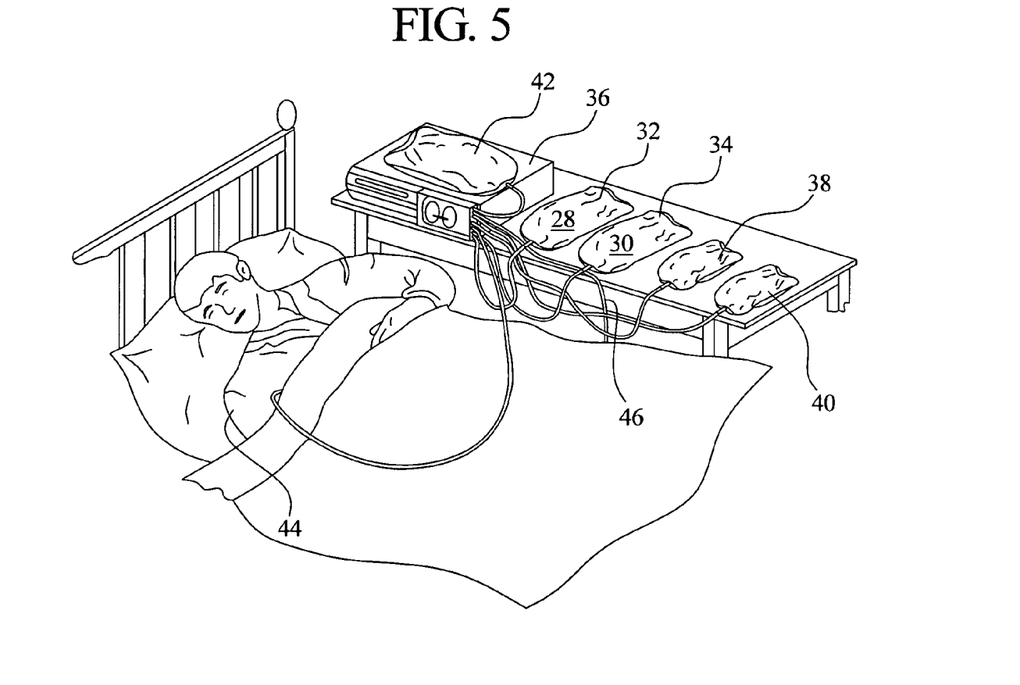
FIG. 5 is a schematic representation of an automated peritoneal dialysis therapy utilizing the dialysis solutions pursuant to an embodiment of the present invention.

In another embodiment, the dextrose concentrate and the buffer concentrate can be prepared and stored in separate containers and then mixed via an admix device prior to use, such as applied during automated peritoneal dialysis. As shown in FIG. 5, the dextrose concentrate 28 and the buffer concentrate 30 are stored in respective separate containers 32 and 34 or bags which are fluidly connected to an admix device 36 suitable for use during automated peritoneal dialysis, an example of which includes ADMIX HOMECHOICE by BAXTER INTERNATIONAL, INC. In addition to the dextrose and buffer concentrates, a first bag 38 and last bag 40 filled with a suitable solution can also be used during dialysis therapy as generally known.

In an embodiment, an effective amount of the dextrose concentrate 28 and the buffer concentrate 30 are drawn from each respective container and into a heater bag 42 where the dextrose and buffer concentrates can be mixed and heated prior to infusion into a patient 44 during dialysis therapy. As further shown in FIG. 5, a drain line 46 is coupled to the admix device 36 from which waste fluids can be removed from the patient during therapy.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A dialysis solution comprising:
   a first acidic solution including a dextrose concentrate and having a pH ranging from about 2.8 to about 3.8; and
   a second acidic solution including a buffer concentrate wherein the first acidic solution and the second acidic solution are admixed to form a ready-to-use dialysis solution, and wherein the second acidic solution has pH of less than 5.5.

2. The dialysis solution of claim 1 wherein the dextrose concentrate includes, dextrose, calcium chloride, and magnesium chloride.

3. The dialysis solution of claim 1 wherein the buffer concentrate includes a lactate-based Concentrate.

4. The dialysis solution of claim 1 wherein the ready-to-use dialysis solution includes about 1.5% to about 4.25% of dextrose.

5. The dialysis solution of claim 1 wherein the ready-to-use dialysis solution includes sodium and about 2.5 mEq/L to about 3.5 mEq/L of calcium.

6. The dialysis solution of claim 1 wherein the ready-to-use dialysis solution includes about 40 mEq/L of lactate.

7. A two part peritoneal dialysis solution comprising:
   a first part including an acidic concentrate having a pH from about 2.8 to about 3.8 that includes dextrose; and
   a second part including a lactate-based buffer concentrate having a pH of less than 5.5 wherein the first part and the second part are admixed prior to infusion into a patient.

8. The two part peritoneal dialysis solution of claim 7 wherein the pH of the first part ranges from about 3.0 to about 3.5.

9. The two part peritoneal dialysis solution of claim 7 wherein the acidic concentrate further includes calcium chloride and magnesium chloride.

10. The two part peritoneal dialysis solution of claim 7 wherein the lactate-based buffer concentrate has pH that ranges from about 5.0 to less than 5.5.

11. The two part peritoneal dialysis solution of claim 7 wherein the acidic concentrate includes about 30.0 g/L to about 85.0 g/L of dextrose, calcium chloride dihydrate, and magnesium chloride hexahydrate.

12. The two part peritoneal dialysis solution of claim 11 wherein the acidic concentrate includes about 7.0 mEq/L of calcium.

13. The two part peritoneal dialysis solution of claim 11 wherein the acidic concentrate includes about 5.0 mEq/L of calcium.

14. The two part peritoneal dialysis solution of claim 7 wherein the lactate-based buffer concentrate includes sodium chloride and sodium lactate.

15. A two part peritoneal dialysis solution comprising:
   a first part housed in a first structure, the first part including an acidic dextrose concentrate having a pH of about 2.8 to about 3.8; and
   a second part housed in a second structure, the second part including an acidic buffer concentrate wherein the first part and the second part are separately sterilized and admixed to form a ready-to-use peritoneal dialysis solution, and wherein the second part has a pH that is less than 5.5.

16. The two part peritoneal dialysis solution of claim 15 wherein the first part and the second part are stored in a multi-chamber container including the first structure and the second structure adaptedly coupled such that the first pan and the second part are capable of mixing to form the mixed solution prior to infusion into the patient.

17. The two part peritoneal dialysis solution of claim 15 wherein the first structure and the second structure each include a solution bag capable of being coupled to an admix device allowing mixing of the first part and the second part to form the mixed solution.

18. The two part peritoneal dialysis solution of claim 15 wherein the ready-to-use peritoneal dialysis solution includes about 1.5% to about 4.25% of dextrose.

19. The two part peritoneal dialysis solution of claim 18 wherein the ready-to-use peritoneal dialysis solution further includes sodium, calcium, chloride, magnesium and lactate.

20. The two part peritoneal dialysis solution of claim 15 wherein the acidic dextrose concentrate includes dextrose, calcium chloride and magnesium chloride.

21. A method of producing a dialysis solution, the method comprising the steps of:
   formulating an acidic concentrate and a buffer concentrate having a pH of less than 5.5 wherein the acidic concentrate at least includes dextrose and having a pH of about 2.8 to about 3.8;
   separately sterilizing the acidic concentrate and the buffer concentrate; and
   mixing the acidic concentrate and the buffer concentrate.

22. The method of claim 21 wherein the acidic concentrate and the buffer concentrate are each housed in a respective chamber of a multi-chambered container adaptedly coupled such that the acidic concentrate and the lactate-based buffer concentrate can be mixed within the multi-chambered container.

23. The method of claim 21 wherein the acidic concentrate and the buffer concentrate are each housed in a respective solution bag each capable of being coupled to an admix device allowing mixing of the acidic concentrate and the lactate-based buffer concentrate.

24. The method of claim 21 wherein the acidic concentrate further includes calcium chloride and magnesium chloride.

25. The method of claim 21 wherein the buffer concentrate includes a lactate-based concentrate at a pH that ranges from about 5.0 to less than 5.5.

26. A method of modifying a standard dialysis solution comprising the steps of:
   formulating two or more solution parts of the standard dialysis solution wherein the solution parts at least include a dextrose concentrate and a buffer concentrate;
   separately sterilizing the dextrose concentrate at a pH of 2.8 to about 3.8 and the buffer concentrate at a pH of less than 5.5; and
   mixing the dextrose concentrate and the buffer concentrate to produce a modified standard dialysis solution.

27. The method of claim 26 wherein the modified standard dialysis solution includes fewer glucose degradation products than the standard dialysis solution.

28. The method of claim 27 wherein the glucose degradation products are selected from the group consisting of 5-hydroxymethyl furfural, 3-deoxyglucasone, glyoxal, methylglyoxal, acetaldehyde and combinations thereof.

29. The method of claim 26 wherein the modified standard dialysis solution includes a solution composition that is substantially the same as the standard dialysis solution except for the glucose degradation products.

30. The method of claim 26 wherein the modified standard dialysis solution includes about 1.5% to about 4.25% of dextrose.

31. The method of claim 26 wherein the modified standard dialysis solution further includes sodium, calcium, magnesium, chloride, and lactate.

32. The method of claim 26 wherein the buffer concentrate includes a lactate-based concentrate.

33. The method of claim 32 wherein the lactate-based Concentrate includes sodium lactate and sodium chloride.

34. The method of claim 26 wherein the dextrose concentrate includes dextrose, calcium chloride and magnesium chloride.

35. A method of providing dialysis to a patient comprising the steps of:

mixing an acidic dextrose concentrate and an acidic buffer solution to form a ready-to-use dialysis solution wherein the acidic dextrose concentrate and the acidic buffer concentrate are separately sterilized prior to mixing and wherein the acidic buffer concentrate has a pH that is less than 5.5 and the acidic dextrose concentrate has a pH of from about 2.8 to about 3.8; and using the ready-to-use dialysis solution during dialysis.

36. The method of claim 35 wherein the ready-to-use dialysis solution is used as a dialysate.

37. The method of claim 35 wherein the ready-to-use dialysis solution is infused into the patient during peritoneal dialysis.

38. The method of claim 35 wherein the acidic dextrose concentrate includes dextrose, calcium chloride, and magnesium chloride.

* * * * *